United States Patent [19]

Dean

[11] Patent Number: 5,614,653

[45] Date of Patent: Mar. 25, 1997

[54] SOLUBILIZATION OF BORIC ACID

[75] Inventor: Frank W. Dean, Spring, Tex.

[73] Assignee: Stoller Enterprises, Inc., Houston, Tex.

[21] Appl. No.: 420,081

[22] Filed: Apr. 11, 1995

[51] Int. Cl.$^6$ .............................. C07F 19/00; C07F 5/02; C07F 1/08

[52] U.S. Cl. ................................... 556/7; 71/64.1; 556/8; 556/133; 556/134; 556/148; 556/149

[58] Field of Search .................................... 556/7, 8, 133, 556/134, 148, 149

[56] References Cited

U.S. PATENT DOCUMENTS

| | | | |
|---|---|---|---|
| 2,999,064 | 9/1961 | Sluhan | 252/34.7 |
| 3,186,946 | 6/1965 | Sluhan | 252/49.3 |
| 4,007,029 | 2/1977 | Kenton | 71/11 |
| 4,155,739 | 5/1979 | Downer et al. | 71/27 |
| 4,332,609 | 6/1982 | Ott | 71/27 |
| 4,461,721 | 7/1984 | Goettsche et al. | 252/607 |
| 4,572,733 | 2/1986 | Howard | 71/64.08 |
| 4,844,725 | 7/1989 | Malouf et al. | 71/3 |

Primary Examiner—Porfirio Nazario-Gonzalez
Attorney, Agent, or Firm—Browning Bushman

[57] ABSTRACT

The present invention is directed to methods for solubilizing boric acid to produce liquid, boron-containing solutions. In these methods, boric acid is added to a previously formed solution of a metal ion and ligand. The ligand must be capable of both complexing the metal ion and simultaneously coordinating or hydrogen bonding with the boric acid. Preferred metal ions are the transition metals. Preferred ligands are the alkanolamines, polyamines, dialkylaminoalkylamines and alkyldiaminecarboxylic acids and salts thereof. Using the methods of the present invention, stable, clear solutions, preferably aqueous solutions, containing about 9–11 percent-by-weight or more boron are readily prepared.

25 Claims, No Drawings

SOLUBILIZATION OF BORIC ACID

BACKGROUND OF THE INVENTION

1. Field of the Invention

The present invention generally relates to methods for solubilizing boric acid and to boric acid solutions prepared by those methods. More specifically, the present invention is directed to methods particularly useful for preparing aqueous boric acid solutions containing about one pound boron per gallon of solution for use as fertilizer concentrates.

2. Description of the Background

Boric acid forms white, needlelike crystals in which the $B(OH)_3$ units are linked together by hydrogen bonds to form layers of nearly hexagonal symmetry. These boric acid crystals are not very soluble. In fact, the solubility of boric acid in cold water is only about 63.5 grams/liter at room temperature. Thus, saturated aqueous solutions of boric acid can contain no more than about one percent-by-weight boron.

As liquid compositions containing soluble boron have become increasingly popular as fertilizers, those skilled in the art have been interested in methods for increasing the solubility of boron. Because boric acid contains only about 18 percent-by-weight boron, the concentration of boron in solution is limited. However, those skilled in the art have been desirous of obtaining liquid solutions containing about 9–11 percent-by-weight boron.

Liquid boron solutions have long been prepared by dissolving an inorganic borate, e.g., sodium borate, in water. Because the borates are not significantly more soluble than boric acid, the maximum concentration of boron which can be achieved with saturated borate solutions is only about three percent-by-weight.

Other attempts to increase the concentration of boron in solution have involved the reaction of boron compounds, e.g., boric acid and the borates, with polyamines and alkanolamines to produce polyborates. Because these polyborates are more soluble in water, aqueous solutions containing higher boron concentrations may be prepared. Because it has been found that the boron in these polyborates is available to plants, polyborate solutions have found use as components of plant fertilizers.

Malouf and Docks have described the preparation of aqueous boron-containing compositions in U.S. Pat. No. 4,844,725. The aqueous boron-containing compositions disclosed by Malouf and Docks include the reaction product of boric acid and an alkylamine, together with an alkanol or alkylene glycol and water. These aqueous solutions have been used as boron sources for fertilizer.

In U.S. Pat. No. 4,332,609, Ott describes a liquid fertilizer composition containing a polyborate compound. The polyborate is prepared by reacting a boric acid compound with an alkanolamine or an aliphatic polyamine in a highly exothermic reaction. The solutions disclosed by Ott have been used for plant fertilization.

Howard described the preparation of another boron-containing composition for agricultural use in U.S. Pat. No. 4,572,733. The composition described by Howard is prepared by forming a solution of a borate in a water miscible glycol solvent, followed by addition of a ground, second boron compound to form a flowable composition containing a fine slurry of borate.

Downer described a spray oil containing boron for use as a foliar fertilizer in U.S. Pat. No. 4,155,739. These compositions are based upon borate esters and include amine-borate ester adducts.

U.S. Pat. No. 4,007,029 discloses liquid fertilizer compositions based upon anhydrous ammonia solutions including trace elements which may include boric acid.

Boron-containing solutions also have been used as wood preservatives and as cutting fluids. In U.S. Pat. No. 4,461,721, Gottsche describes a wood preservative comprising an aqueous paste containing boric acid, an organic amine and a polyborate. An aqueous cutting fluid containing the reaction product of boric acid with an alkanolamine, and preferably including a long chain unsaturated fatty acid, is described by Sluhan in U.S. Pat. No. 2,999,064. Sluhan also describes cutting fluid compositions containing borate salts of alkanolamines or alkanoldiamines in his U.S. Pat. No. 3,186,946.

These and other patents relating to boron-containing solutions are summarized in U.S. Pat. No. 4,844,725 which is incorporated herein by reference.

While polyborates and boric acid/amine complexes are known, the specific methods and compositions of the present invention are unique. These methods and compositions permit the preparation of aqueous solutions characterized by high boron concentrations, while avoiding the highly exothermic reactions leading to the formation of polyborates. No known references have suggested, either directly or indirectly, the novel and non-obvious methods and solutions disclosed and clarimed herein. The novel and non-obvious methods and solutions disclosed and claimed herein have solved the long felt but unfulfilled need in the fertilizer industry for a simple method for preparing aqueous, high concentration boron solutions which are stable during long storage times at ambient temperatures. A further advantage of the methods and solutions disclosed and claimed herein is the inclusion of minor amounts of metal ions, particularly transition metals, which are beneficial for plant growth.

SUMMARY OF THE INVENTION

The present invention is directed to methods for solubilizing boric acid to produce liquid, boron-containing solutions comprising the step of forming a metal ion/ligand-containing solution from a ligand and sufficient metal ion to complex the ligand. The ligand must be capable of both complexing the metal ion and simultaneously coordinating or hydrogen bonding with boric acid. This solution is preferably formed in a solvent, most preferrably water. Boric acid is then dissolved in this solution to produce a liquid, boron-containing solution containing up to about 13 percent-by-weight boron, more preferrably about 9–11 percent-by-weight boron.

The metal ion/ligand-containing complex may be added to the solvent as a preformed complex or may be formed in situ by the separate addition of metal ion and ligand. Preferred metal ions are the transition metals, most preferrably cobalt, nickel, copper, zinc and mixtures thereof.

Preferred ligands include a first functional group comprising a tertiary amine or alcohol and a second functional group comprising an alcohol, amine, amide, imine, imide or carboxylate, provided that at least one of these first and second functional groups should be an amine. Most preferred as ligands are the alkanolamines, polyamines, dialkylaminoalkylamines, alkyldiaminecarboxylic acids, salts of those acids and mixtures thereof. It is believed that these ligands complex with the transition metal at one functional group while providing a second functional group, preferra bly a tertiary amine or alcohol, for coordinating or hydrogen bonding with the boric acid.

Solutions containing up to about 75 percent-by-weight boric acid may be prepared using the methods of the present invention. The molar ratio of boric acid to ligand in such solutions may be from about 4:1 to about 9:1.

DETAILED DESCRIPTION OF THE PREFERRED EMBODIMENT

The present invention provides methods for solubilizing boric acid to produce boric acid solutions containing up to about 13 percent-by-weight or more boron. Most preferably, the methods of the present invention are employed to produce aqueous solutions comprising about 9–11 percent-by-weight boron. These solutions are particularly useful as fertilizer concentrates providing about one pound of boron per gallon of solution. These solutions are further advantageous to deliver small quantities of micronutrients, including transition metals, and nitrogen from ligands containing amine functional groups.

The methods for solubilizing boric acid described below have been found particularly advantageous because they avoid the high temperatures resulting from the exothermic reactions described by Ott and others in the formation of polyborates. Because these high temperatures are avoided, solutions containing high boron concentrations may be prepared and packaged quickly and easily without requiring cooling of the polyborate solutions. While some heat is given off during the preparation of the metal ion/ligand-containing intermediate solution, Applicant has recognized that addition of boric acid to this solution actually reduces the temperature thereof. Clear, stable, high concentration boron solutions may be quickly and easily prepared and packaged in a commercial operation without requiring cooling delays.

A liquid boron-containing solution in accord with the present invention comprises boric acid, a metal ion and a ligand capable of both complexing the metal ion and coordinating or hydrogen bonding with boric acid. Preferably, the metal ion comprises a transition metal, most preferably cobalt, nickel, copper, zinc and mixtures thereof. The presently preferred transition metal is copper(II) which may be added in any convenient form, e.g., as copper chloride. Sufficient metal ion must be included to complex the ligand. It has been found that solutions containing from about 0.5 to about 2.0 percent-by-weight metal ion normally are sufficient.

While the actual solubilizing mechanism is not clear, it is believed that the ligand, having two functional groups, complexes at one functional group with the transition metal ion while providing a second functional group for coordinating or hydrogen bonding with the boric acid. The preferred functional group for coordinating with the boric acid is believed to be a tertiary amine or alcohol. These functional groups may serve as a Lewis base by providing an unshared pair of electrons for sharing through hydrogen bonding with the boric acid. While the preferred functional groups are the tertiary amines and alcohols, it is believed more generally that unshared electrons on a nitrogen, oxygen, phosphorous or sulphur of a functional group may serve the required function.

While the ligand is often a liquid and may serve as the solvent for the liquid boron-containing solution, it is preferred, particularly for agricultural use, that the solution include water as the solvent. While boric acid may comprise up to about 75 percent-by-weight of the solution, the solution will preferably contain from about 5 to about 75 percent-by-weight boric acid, most preferably from about 45 to about 55 percent-by-weight boric acid. The molar ratio of boric acid to ligand may be as high as from about 4:1 to about 9:1. These high quantities of boric acid will generally be solubilized in solutions including from about 10 to about 45 percent-by-weight ligand.

Broadly, the ligand should have two functional groups, one capable of complexing the transition metal while the other is capable of coordinating or hydrogen bonding with boric acid. While it is believed that a ligand having any functional group with an unshared pair of electrons on a nitrogen, oxygen, phosphorous or sulphur is capable of coordinating with the boric acid, it is preferred that the functional group be selected from the alcohols, amines, amides, imines, imides and carboxylates. Most preferably, the functional group available for coordinating with boric acid should be a tertiary amine or alcohol. Amines seem to provide the most preferred functional group for complexing with the metal ion. The preferred ligands include the alkanolamines, polyamines, alkyldiaminecarboxylic acids, salts of those acids and mixtures thereof. Presently more preferred ligands include monomethanolamine, monoethanolamine, dimethylaminopropylamine, ethylenediaminetetraacetic acid, hydroxyethylenediaminetriacetic acid, salts of those acids and mixtures thereof. The presently most preferred ligands are monoethanolamine and dimethylaminopropylamine.

The transition metal/ligand-containing solution must be formed prior to addition of boric acid. While it is preferred to prepare this solution in situ, most preferably by the addition to water of a metal salt, followed by the ligand, a metal ion/ligand complex may be preformed. A preformed complex then simply may be dissolved in the solvent, preferably water, prior to addition of boric acid to the solution containing the metal ion/ligand complex.

The present invention will be more fully understood from examination of the following specific examples.

Example 1

Six grams of copper chloride dihydrate ($CuCl_2 \cdot 2H_2O$) was dissolved in 334 grams of water. 140 grams of dimethylaminopropylamine (DMAPA) was blended into this solution with the release of some heat. As the copper was complexed, the solution turned from green to a very intense, dark blue. The temperature of this solution rose to about 120° F. To this solution was added 520 grams of boric acid. With stirring, all of the boric acid went into solution within about five minutes during which time the temperature dropped by about 20° F. or more. The resulting solution was a clear, intense, dark blue. The resulting solution comprised about 9 percent-by-weight boron and remained stable through an extended storage at room temperature. The solution was characterized by a specific gravity of about 1.25 and a pH of about 7.2. The percentages of components, the boric acid to ligand ratio and the boron concentration are listed in Table I.

TABLE I

|  | Example 1 | Example 2 | Example 3 | Example 4 |
|---|---|---|---|---|
| Water (%) | 33.4 | 33.4 | 31.1 | 5.0 |
| $CuCl_2 \cdot 2H_2O$ (%) | 0.6 | 1.0 | 0.6 | 0.6 |

TABLE I-continued

|  | Example 1 | Example 2 | Example 3 | Example 4 |
|---|---|---|---|---|
| DMAPA (%) | 14.0 | 13.6 | 14.4 | 20.0 |
| Boric Acid (%) | 52.0 | 52.0 | 53.9 | 74.4 |
| Boric Acid:Ligand (Molar Ratio) | 6.12 | 6.28 | 6.31 | 6.16 |
| Boron (%) | 9.09 | 9.09 | 9.43 | 13.0 |

Examples 2–4

Additional examples using different percentages of the same constituents were prepared following the method set forth in Example 1. The percentages of constituents for these examples are listed in Table I. These examples all produced clear, intense, dark blue solutions. Examples 2 and 3 corroborate the results of Example 1. Example 4 illustrates the preparation of a more concentrated solution having about 13.0 percent-by-weight boron.

Comparative Example 1

A comparative example was performed to illustrate the effect which results from the absence of the metal ion. 88 grams of ethylenediamine and 520 grams of boric acid were blended into 300 grams of water. A solid was quickly formed and precipitated.

Comparative Example 2

A comparative example was peformed to investigate the effect of late addition of the metal ion after boric acid and a polyamine have had an opportunity to react. 137 grams of DMAPA were blended into 343 grams of water. To this mixture was added 520 grams of boric acid. A clear solution having a pH of about 7.65 and a specific gravity of about 1.25 was produced with the evolution of much heat. After the solution cooled to room temperature and within two days, a salt formed and precipitated out. Addition of 6 grams of copper chloride dihydrate when the precipitate was first observed failed to prevent or retard the salt formation and precipitation.

The production of a clear solution with evolution of significant heat suggests that the boric acid and DMAPA had reacted to form a polyborate which then began to precipitate out. After such a reaction, the addition of the copper ion could not prevent salt formation and precipitation.

Comparative Example 3

The method of Example 1 was repeated with the exception that monoisopropylamine, an amine having a single functional group, was substituted for the DMAPA. To 334 grams of water were added 6 grams of copper chloride dihydrate and 140 grams of monoisopropylamine. The solution remained green; it did not develop the intense, dark blue color characteristic of the copper complex of Example 1. To this solution was added 520 grams of boric acid. Even with vigorous stirring, little, if any, of the boric acid would go into solution.

This example illustrates the apparent necessity for the ligand to have at least two functional sites, one to complex with the metal ion and another to coordinate or hydrogen bond with the boric acid.

The comparative examples are summarized in Table II.

TABLE II

|  | Comp. Ex. 1 | Comp. Ex. 2 | Comp. Ex. 3 |
|---|---|---|---|
| Water (%) | 33.0 | 34.3 | 33.4 |
| $CuCl_2 \cdot 2H_2O$ (%) | — | — | 0.6 |
| DMAPA (%) | — | 13.7 | — |
| EDA (%) | 9.7 | — | — |
| MPA (%) | — | — | 14.0 |
| Boric Acid (%) | 57.3 | 52.0 | 52.0 |

Example 5

The procedure of Example 1 was repeated with the exception that the ligand was monoethanolamine and different percentages of the various constituents were employed. The component percentages are listed in Table III. A clear, intense, dark blue solution was produced having a pH of about 8.0.

TABLE III

|  | Example 5 | Example 6 |
|---|---|---|
| Water (%) | 24.7 | 32.5 |
| $CuCl_2 \cdot 2H_2O$ (%) | 0.3 | 1.2 |
| DMAPA (%) | — | 9.3 |
| MEA (%) | 20.0 | — |
| Versene-220 (%) | — | 7.0 |
| Boric Acid (%) | 55.0 | 50.0 |

Example 6

The procedure of Example 1 was repeated with the exception that Versene-220, a commercially available solution of the tetrasodium salt of ethylenediaminetetraacetic acid, was used as the ligand. A clear, intense, dark blue solution having a pH of about 6.8 was produced. See Table III for the details of this example.

The foregoing examples illustrate that boric acid may be readily solubilized by the methods of the present invention to produce clear solutions containing about 9–13 percent-by-weight boron. The evolution of excessive heat, characteristic of the production of polyborates is avoided. Solutions prepared in accord with the present invention have been found to remain clear and stable for extended periods of time at room temperature.

The comparative examples illustrate the necessity of forming the metal ion/ligand complex before addition of boric acid. Further, the comparative examples illustrate the necessity of employing both a metal ion and a ligand having at least two functional groups, one capable of complexing with the metal ion while the other simultaneously coordinates or hydrogen bonds with the boric acid.

The foregoing description of the invention has been directed in primary part to particular preferred embodiments in accordance with the requirements of the patent statutes and for purposes of explanation and illustration. It will be apparent, however, to those skilled in the art that many modifications and changes in the specifically described methods and solutions may be made without departing from the true spirit and scope of the invention. In particular, it is not intended that the present invention be restricted to the particular, preferred ligands and metal ions listed, but that all metal ions and ligands having the required characteristics should be included. Further, other variations, including the addition of heat, if desired, during the solubilization process may be employed. Therefore, the invention is not restricted to the preferred embodiments described but covers all modifications which may fall within the scope of the following claims.

What is claimed is:

1. An aqueous boron-containing solution, comprising
   about 5 to about 75 percent-by-weight boric acid;
   about 10 to about 45 percent-by-weight ligand selected from the group consisting of alkanolamines, dialkylaminoalkylamines, alkyldiaminecarboxylic acids, salts of said acids and mixtures thereof;
   sufficient transition metal ion to complex said ligand; and
   the balance water.

2. The boron-containing solution of claim 1 wherein said ligand is selected from the group consisting of monomethanolamine, monoethanolamine, dimethylaminopropylamine, ethylenediaminetetraacetic acid, hydroxyethylenediaminetriacetic acid, salts of said acids and mixtures thereof and said transition metal is selected from the group consisting of cobalt, nickel, copper, zinc and mixtures thereof.

3. The boron-containing solution of claim 2 comprising about 45 to about 55 percent-by-weight boric acid, wherein the molar ratio of said boric acid to said ligand is about 4:1 to about 9:1 said ligand is dimethylaminopropylamine and said transition metal ion is copper.

4. An aqueous boron-containing solution, comprising:
   water;
   boric acid; and
   a water soluble complex of a transition metal ion and a ligand capable of both complexing said transition metal ion and hydrogen bonding with said boric acid.

5. The boron-containing solution of claim 4 wherein said complex is formed in situ in said water.

6. The boron-containing solution of claim 4 wherein said ligand includes a functional group selected from the group consisting of the tertiary amines and alcohols.

7. The boron-containing solution of claim 6 wherein said ligand further includes a second functional group selected from the group consisting of the alcohols, amines, amides, imines, imides and carboxylates and at least one of said first or second functional groups is an amine.

8. The boron-containing solution of claim 4 wherein the molar ratio of boric acid to ligand is from about 4:1 to about 9:1.

9. A liquid boron-containing solution, comprising:
   boric acid;
   a transition metal ion;
   a ligand capable of both complexing said transition metal ion and coordinating with said boric acid as a Lewis base.

10. The boron-containing solution of claim 9 wherein said ligand includes a Lewis base functional group wherein an unshared pair of electrons is available on an element selected from the group consisting of nitrogen, oxygen, phosphorous and sulfur.

11. The boron-containing solution of claim 10 wherein said ligand further includes a second functional group selected from the group consisting of the alcohols, amines, amides, imines, imides and carboxylates.

12. The boron-containing solution of claim 9 wherein the molar ratio of boric acid to ligand is from about 4:1 to about 9:1.

13. The boron-containing solution of claim 9 further comprising a solvent.

14. A water-soluble complex, comprising:
   boric acid;
   a transition metal ion; and
   a ligand capable of both complexing said transition metal ion and coordinating with said boric acid.

15. The water-soluble complex of claim 14 wherein said ligand includes a Lewis base functional group selected from the group consisting of nitrogen, oxygen, phosphorous and sulfur.

16. The water-soluble complex of claim 15 wherein said ligand further includes a second functional group selected from the group consisting of the alcohols, amines, amides, imines, imides and carboxylates.

17. The water-soluble complex of claim 14 wherein the molar ratio of boric acid to ligand is from about 4:1 to about 9:1.

18. The water-soluble complex of claim 14 wherein said ligand is selected from the group consisting of alkanolamines, polyamines, alkyldiaminecarboxylic acids, salts of said acids and mixtures thereof.

19. An aqueous, boron-containing solution comprising an aqueous solution of a complex selected from the group consisting of the complexes described in foregoing claims 14–18.

20. The boron-containing solution of claim 19 wherein said complex is formed in situ in said aqueous solution.

21. A method for solubilizing boric acid to produce a liquid, boron-containing solution, comprising:
   forming a metal ion/ligand-containing solution from a ligand and sufficient metal ion to complex said ligand, said ligand capable of both complexing said metal ion and coordinating with boric acid; and
   adding boric acid to said metal ion/ligand-containing solution.

22. The method of claim 21 comprising forming said solution in a solvent.

23. The method of claim 22 wherein said solvent is water and said boric acid is added in an amount sufficient to comprise about 5 to about 75 percent-by-weight of said boron-containing solution and to produce a molar ratio of boric acid to ligand of from about 4:1 to about 9:1.

24. The method of claim 22 wherein said metal ion and ligand are added to said solvent as a preformed complex.

25. The method of claim 22 wherein said metal ion/ligand complex is formed in situ in said solution.

* * * * *